(12) United States Patent
Ooyatsu

(10) Patent No.: US 7,828,722 B2
(45) Date of Patent: Nov. 9, 2010

(54) ENDOSCOPE

(75) Inventor: Masayuki Ooyatsu, Saitama (JP)

(73) Assignee: Fujinon Corporation, Saitama (JP)

( * ) Notice: Subject to any disclaimer, the term of this patent is extended or adjusted under 35 U.S.C. 154(b) by 1133 days.

(21) Appl. No.: 11/338,755

(22) Filed: Jan. 25, 2006

(65) Prior Publication Data
US 2006/0167341 A1 Jul. 27, 2006

(30) Foreign Application Priority Data
Jan. 25, 2005 (JP) ............................ P.2005-016649

(51) Int. Cl.
*A61B 1/04* (2006.01)
(52) U.S. Cl. ....................... 600/130; 600/129; 600/109; 600/178
(58) Field of Classification Search ................ 600/109, 600/139, 130, 146, 149, 153, 160, 176, 177, 600/182, 129
See application file for complete search history.

(56) References Cited

U.S. PATENT DOCUMENTS

| 4,622,954 A | | 11/1986 | Arakawa et al. | |
|---|---|---|---|---|
| 4,706,656 A | * | 11/1987 | Kuboto | ........................ 600/153 |
| 4,757,805 A | | 7/1988 | Yabe | |
| 4,809,680 A | * | 3/1989 | Yabe | ........................... 600/130 |
| 4,918,521 A | * | 4/1990 | Yabe et al. | ................... 600/109 |
| 5,376,960 A | | 12/1994 | Wurster | |
| 5,454,366 A | * | 10/1995 | Ito et al. | ....................... 600/109 |
| 2002/0123664 A1 | * | 9/2002 | Mitsumori | ................... 600/130 |

FOREIGN PATENT DOCUMENTS

| JP | 63-113415 A | 5/1988 |
|---|---|---|
| JP | 5-6456 B2 | 1/1993 |
| JP | 2002-58632 A | 2/2002 |
| JP | 2004-254729 A | 9/2004 |

OTHER PUBLICATIONS

Japanese Office Action of Apr. 19, 2010 for Application No. 2005-016649.

* cited by examiner

*Primary Examiner*—John P Leubecker
*Assistant Examiner*—Victoria W Chen
(74) *Attorney, Agent, or Firm*—Birch Stewart Kolasch & Birch, LLP

(57) ABSTRACT

Where two axes X and Y using the axial center position as the origin are set on a section orthogonal to the axial line of the distal end hard portion, the observation portion and the treatment equipment lead-out portion are disposed at both side positions between which the Y-axis is placed, the surface on which the solid-state image pickup device of the substrate is incorporated is disposed in a direction parallel to the X-axis, the center of the treatment equipment lead-out port is disposed between a plane parallel to the X-axis including the center of the optical axis of the object lens and a plane including the plane of the substrate, the line connecting the centers of both the illumination portions are roughly parallel to the Y-axis, and is drawn near the center of the optical axis of the object lens, and the distances between the center of the optical axis and both the illumination portions are made as equal to each other as possible.

3 Claims, 4 Drawing Sheets

ENDOSCOPE

BACKGROUND OF THE INVENTION

1. Field of the Invention

The present invention relates to an endoscope used in the medical field, and in particular to an endoscope, the insertion portion of which is made small in diameter.

2. Description of the Related Art

An endoscope is composed so that the insertion portion inserted into a body cavity is connected to the body control portion held by hands and operated by an operator, and a universal cord detachably connected to a light source unit and a processor is led out from the body control portion. The endoscope observation means consisting of an illumination portion and an observation portion is attached to the distal end of the insertion portion, by which inspections and diagnoses are carried out in a body cavity. In addition, a treatment equipment lead-out port for leading out forceps and treatment equipment are provided at a position adjacent to the endoscope observation means in order to apply a treatment to an affected part. An injection nozzle, etc., for a rinsing fluid to rinse an observation portion is further mounted at the distal end of the insertion portion.

Herein, an illumination portion to illuminate the inside of a body cavity is provided, as described above, in addition to the observation portion because the inside of a body cavity is dark. The illumination portion is composed by mounting an illumination lens to the distal end of the light guide led from the universal cord to the inside of the insertion portion via the body control portion. However, it is necessary to irradiate uniform illumination light to as a wide area as possible from the illumination portion. Therefore, the illumination portion is provided with at least two points and is disposed at both sides between which the observation portion is placed. The observation portion is provided with an object optical system including an object lens and a solid-state image pickup device. The solid-state image pickup device is incorporated on a substrate to which a predetermined number of wires are connected. Accordingly, since the solid-state image pickup device has a large size, it will occupy a wide space if it is disposed in the direction orthogonal to the axial line of the insertion portion. Therefore, the solid-state image pickup device and the substrate thereof are disposed so as to be oriented in the axial direction of the insertion portion. And, a prism is provided, which bends the optical axis of the object lens oriented in the axial direction of the insertion portion by 90°.

Forceps, radio frequency treatment equipment, or appropriate treatment equipment in compliance with a purpose and use is inserted into the treatment equipment lead-out port, and treatment such as extraction of an affected part is carried out. A treatment equipment insertion channel that becomes a path of the treatment equipment is connected to the treatment equipment lead-out port. The treatment equipment insertion channel is led to the body operation portion and reaches the treatment equipment lead-in portion secured at the body control portion.

Therefore, in order to improve efficiency and function of treatment by the endoscope observation means, the inner diameter of the treatment equipment insertion channel and the pore diameter of the treatment equipment lead-out port are made as large as possible, and it is necessary to lead out large-sized treatment equipment. On the other hand, since the insertion portion of the endoscope is inserted into a body cavity of a patient and it is necessary to pass the insertion portion through a narrow portion in the insertion channel, it is favorable that the outer diameter dimension of the insertion portion is made as small as possible in order to relieve the burden of a patient and to improve the insertion efficiency. Therefore, such an endoscope is proposed by JP-B-5-6456, which is composed so that, by setting the object optical system and solid-state image pickup device so as to take a predetermined positional relationship with respect to the treatment equipment insertion channel, thinning in the diameter of the insertion portion is attempted, and simultaneously the treatment equipment insertion channel is made large.

According to JP-B-5-6456, the endoscope is composed so that the optical axis of the object optical system, secured at the distal end composition of the insertion portion, which composes the observation system is bent roughly orthogonally, and an image is formed on a solid-state image pickup device, a plane passing through the center axis of the object optical system and parallel to the solid-state image pickup device is positioned in the vicinity of the center axis of the treatment equipment insertion channel. In summary, the optical axis of the object optical system is bent by 90° by using a prism and an image is formed on the solid-state image pickup device. Therefore, with respect to the widest solid-state image pickup device among the respective members disposed at the distal end of the insertion portion, the treatment equipment insertion channel being the next largest member is offset equivalently to the distance between the solid-state image pickup device and the center position of the object optical system, wherein it is possible to effectively utilize the space at the distal end of the insertion portion, and possible to make large the inner diameter of the treatment equipment insertion channel.

Although, in the composition of JP-B-5-6456, great importance is attached to the positional relationship between the observation portion consisting of the object optical system and the solid-state image pickup device and the treatment equipment insertion channel, the members incorporated in the endoscope are not limited thereto, wherein many other components are provided. In particular, arrangement of the illumination portion that composes the endoscope observation means greatly influences, along with the observation, the quality of images showing the inside of a body cavity, which is obtained by the observation portion. Idealistically, it is necessary that illumination light is uniformly irradiated without unevenness onto the entirety of the field of vision of the observation portion For this reason, it is composed that at least two illumination portions are provided, and these two illumination portions are disposed at both sides between which the observation portion is placed, and the line connecting both the centers of both the illumination portions passes through the center of the observation portion or is positioned in the vicinity thereof, and it is necessary that the distances from both the illumination portions to the observation portion are made as equal as possible.

However, the endoscope disclosed in JP-B-5-6456 is composed so that the observation portion and the treatment equipment insertion channel are disposed at a predetermined position at the distal end of the insertion portion, and the illumination portion is disposed in an excess space. Therefore, the line connecting the illumination portions provided with two points is greatly deviated from the center of the observation portion, and the differences between both the illumination portions and the observation portions are great. In JP-B-5-6456, a difference is brought about for the calibrations of both the illumination portions, by which unevenness in illumination is attempted to be reduced. However, unevenness in illumination still occurs. As a result, the quality of an image obtained by the endoscope observation means is lowered, wherein there remains a problem in that the accuracy in inspections and diagnoses is lowered.

SUMMARY OF THE INVENTION

The invention was developed in terms of the above-described points, and it is therefore an object of the invention to provide an endoscope that is attempted to make the diameter of the insertion portion smaller without lowering the functions of respective members incorporated in the insertion by effectively utilizing a space of the distal end of the insertion portion, and can suppress unevenness in illumination, which lowers the quality of observed images.

In order to achieve the above-described object, the invention is featured in that an endoscope comprising: a body control portion; and an insertion portion including a distal end hard portion, the insertion portion being connected to the body control portion, wherein an endoscope observing section and a treatment equipment lead-out port are provided at a distal end surface of the distal end hard portion, the endoscope observing section comprising an illumination portion and an observation portion, and wherein the observation portion comprises: an object optical system comprising an object lens and a prism for bending an optical axis of the object lens by 90° and; a pickup assembly comprising a solid-state image pickup device and a substrate of the solid-state image pickup device, the pickup assembly being connected to the prism, and wherein the illumination portion comprises an illumination lens and a light guide disposed opposite the illumination lens, wherein, when first and second axes orthogonal to each other are established on a section orthogonal to an axial line of the distal end hard portion, the first and second axes centering around an axial center of the distal end hard portion, the pickup assembly is disposed so as to be oriented to a direction parallel to the first axis, and the observation assembly and an observation center of the object lens are disposed opposite each other with the first axis placed therebetween; the treatment equipment lead-out port and the observation portion are disposed opposite each other with the second axis placed as a boundary therebetween; a center of the treatment equipment lead-out port is disposed at a position between a first plane including a surface of a portion, which brings about the maximum width, of the pickup assembly, and a second plane including the observation center of the object lens, the second plane being parallel to the first plane; and the illumination portion is disposed at both sides, between which the object lens is placed, at the side where the object lens is disposed with respect to the second axis.

The composition of the insertion portion is such that a bending portion is connected to the distal end hard portion having the illumination portions and the observation portion provided thereat. The bending portion may be composed so as to bend in two directions including upward and downward or in four directions including upward, downward, leftward and rightward by remote control. Therefore, where the endoscope is composed so as to be provided with an insertion portion having the bending portion, the bending center line in the up and down directions can be set as one axis of two orthogonal axes centering around the axial center of the distal end hard portion, that is, as the X-axis, and the bending center line in the left and right directions may be set as the other axis, that is, as the Y-axis. Whichever of the first axis or the second axis described above may be set as the Y-axis or X-axis. However, in connection to the directivity in the arrangement of the pickup assembly, it is favorable that the first axis described above is regarded as the X-axis, and the second axis is regarded as the Y-axis.

Thus, where the first axis is set as X-axis, the bending direction of the optical axis by means of a prism becomes Y-axis. And, although the pickup assembly and the treatment equipment lead-out port are, respectively, disposed at both sides between which the Y-axis is placed, it is not necessary that these components have completely different areas, but these components may protrude to the other area more or less. In addition, the pickup assembly is composed of an object optical system including an object lens and a prism and a pickup assembly including a solid-state image pickup device and a substrate thereof, and the portion having the maximum width in the pickup assembly becomes a portion where either the solid-state image pickup device or its substrate takes the maximum width. Also, the surface at the maximum width is the light-receiving plane if it is the solid-state pickup element or the conjunction plane of the solid-state pickup element if it is the substrate.

The illumination portion is provided with at least two points, and it is favorable that, only in view of preventing unevenness in the illumination, the center of observation exists on the line connecting the centers of both the illumination portions, and both the illumination portions are equidistant from the center of observation. However, in view of attaching the endoscope observing section having a predetermined dimensional shape to the distal end hard portion, making large-sized the treatment equipment lead-out port, to which the treatment equipment insertion channel is connected, and making the distal end hard portion smaller in diameter, there may be cases where the conditions of the above-described illumination portions cannot be satisfied. Therefore, the treatment equipment lead-out port is made large-sized, the distal end hard portion is made smaller in diameter, the line connecting the centers of both the illumination portions is drawn near the center of observation, and furthermore, the differences in the distance between the center of observation and both the illumination portions are suppressed to a minimum. Accordingly, the positions of both the illumination portions are provided at the side, where the object optical system is disposed, with respect to the Y-axis.

DETAILED DESCRIPTION OF THE INVENTION

Figure 1:
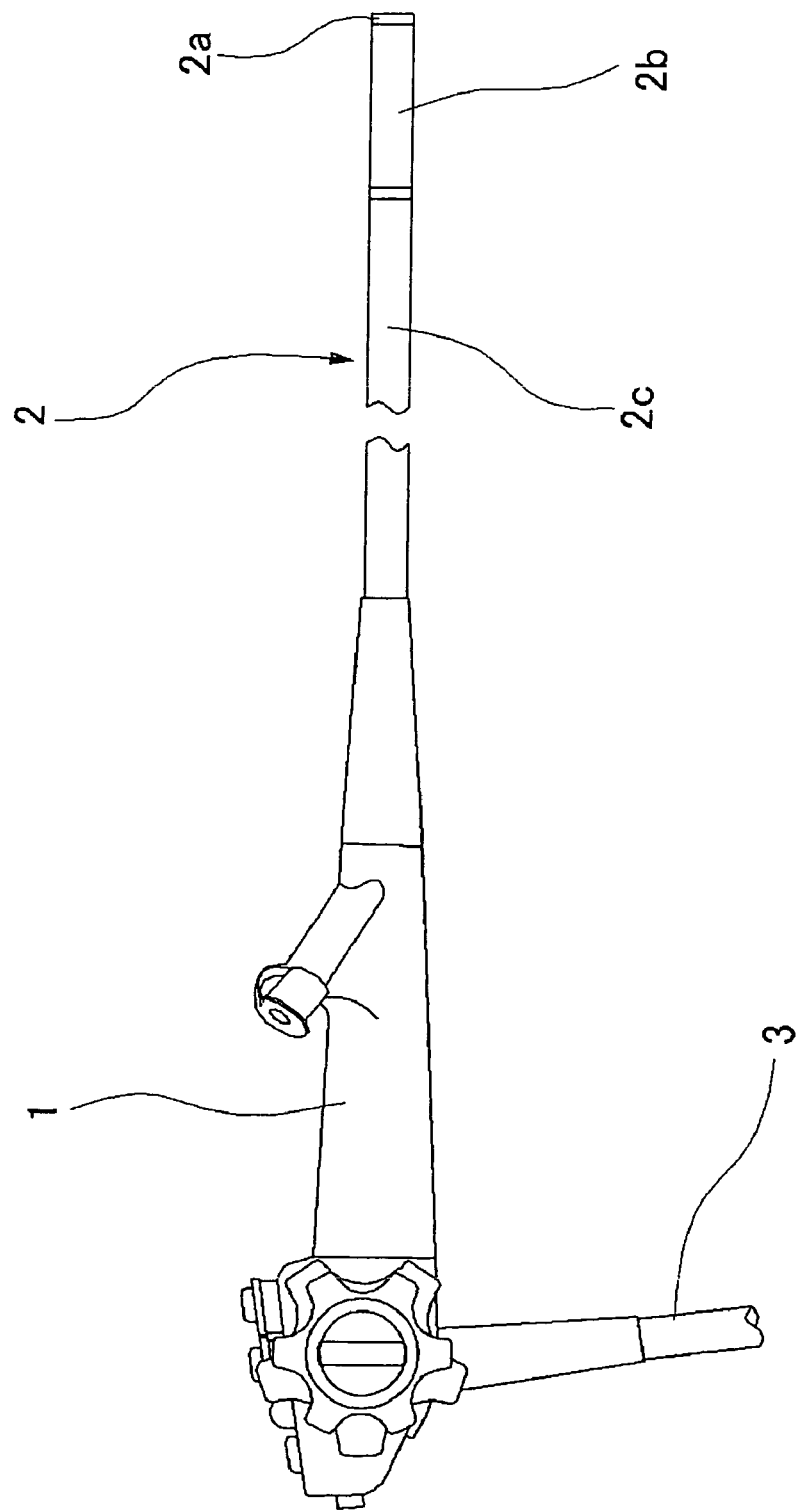
FIG. 1 is an entire configurational view of an endoscope according to the invention.

Hereinafter, a description is given of an embodiment of the invention with reference to the drawings. First, FIG. 1 shows the entirety of an endoscope. In the drawing, reference numeral 1 denotes a body control portion, 2 denotes an insertion portion, and 3 denotes a universal cord. The insertion portion 2 is composed of a distal end hard portion 2a, a bending portion 2b and a flexible portion 2c from its distal end.

Figure 2:
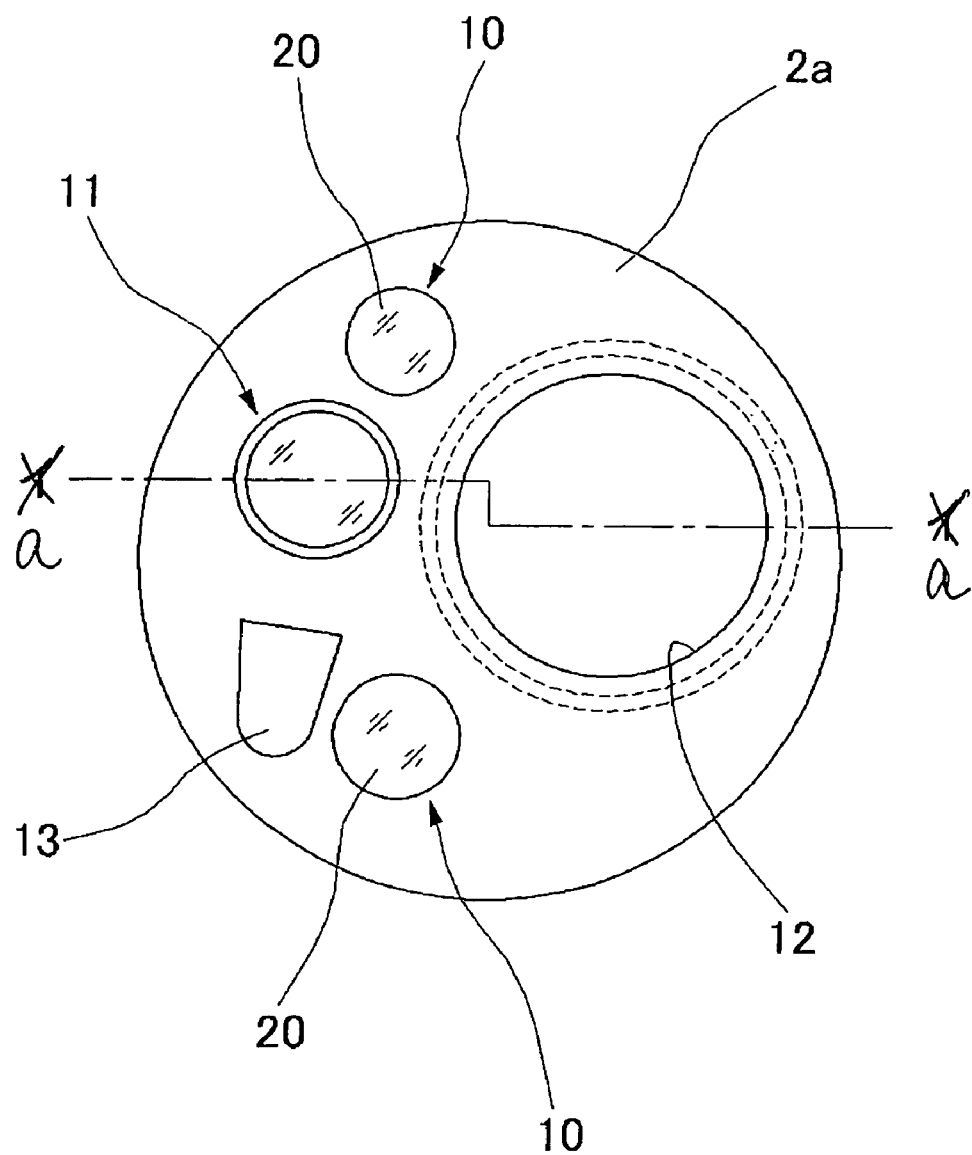
FIG. 2 is a front elevational view depicting the distal end surface of the insertion portion of the endoscope depicted in FIG. 1.
Figure 3:
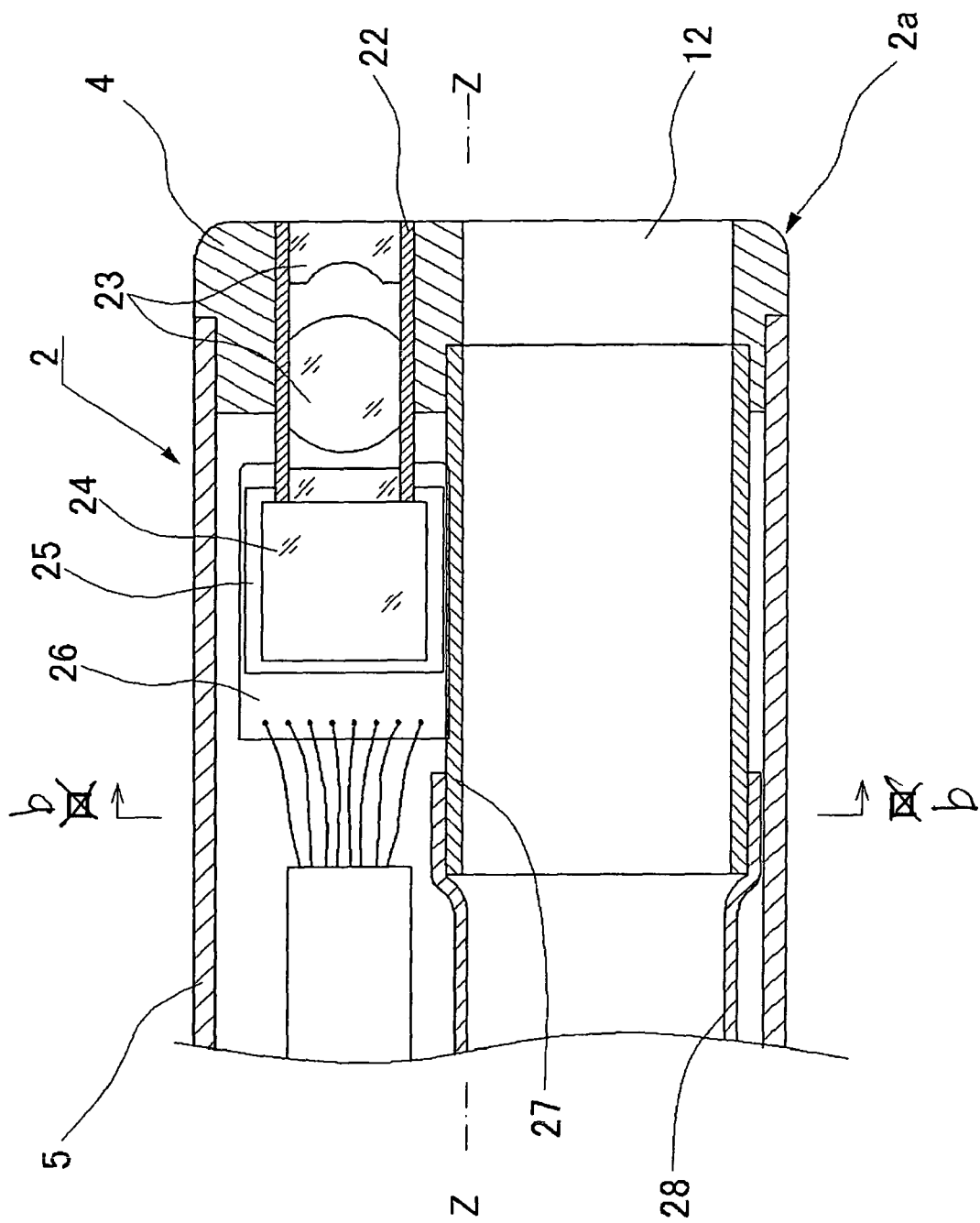
FIG. 3 is a sectional view taken along the line a-a.

FIG. 2 shows the appearance of the distal end surface at the distal end hard portion 2a of the insertion portion 2, and FIG. 3 shows a section of the distal end hard portion 2a. Herein, as has been made clear in FIG. 3, the distal end hard portion 2a is composed of a distal end block 4 and a distal end sleeve 5 fitted to the distal end block 4. And, although the illustration is omitted, a distal end ring at the bending portion 2b is connected to the distal end sleeve 5.

First, in FIG. 2, reference numeral 10 denotes illumination portions provided at two points, 11 denotes an observation portion, 12 denotes a treatment equipment lead-out port, 13 denotes a rinsing nozzle, respectively. These illumination portions 10, the observation portion 11 and the treatment equipment lead-out port 12 are mounted in a through-hole drilled in the distal end block 4 of the distal end hard portion 2a. The respective illumination portions 10 have an illumination lens 20, wherein an emission end of a light guide 21 (Refer to FIG. 4) is faced to each of the illumination lenses 20. In addition, the observation portion 11 is composed of an object optical system and solid-state pickup device, wherein the object optical system includes an object lens 23 mounted in a lens barrel 22, and a prism 24 for bending the optical axis of the object lens 23 by 90°. Also, the pickup assembly includes a solid-state image pickup device 25 and a substrate 26 thereof. The light-receiving plane of the solid-state image pickup device 25 is connected to the prism. The object optical system and the solid-state image pickup device, which compose the observation portion 11 composed as described above, is assembled as a single unit, and is attached to the distal end hard portion 2a.

A linkage pipe 27 is inserted into the treatment equipment lead-out port 12. A treatment equipment insertion channel 28 made of a flexible tube is connected to the linkage pipe 27. Also, the rinsing nozzle 13 communicates with a rinsing fluid passage made of a through-hole, which is provided in the distal end hard portion 2a, and a feed tube 29 (Refer to FIG. 4) is connected to the rinsing fluid passage.

Namely, as it is necessary to be equipped as an endoscope or at least the favorable conditions, it is composed that the insertion portion 2 is made smaller in diameter, the opening diameter from the treatment equipment insertion channel 28 to the treatment equipment lead-out port 12 is attempted to be increased, and unevenness in illumination at the entire observation field of vision of the observation portion 11 is suppressed.

Figure 4:
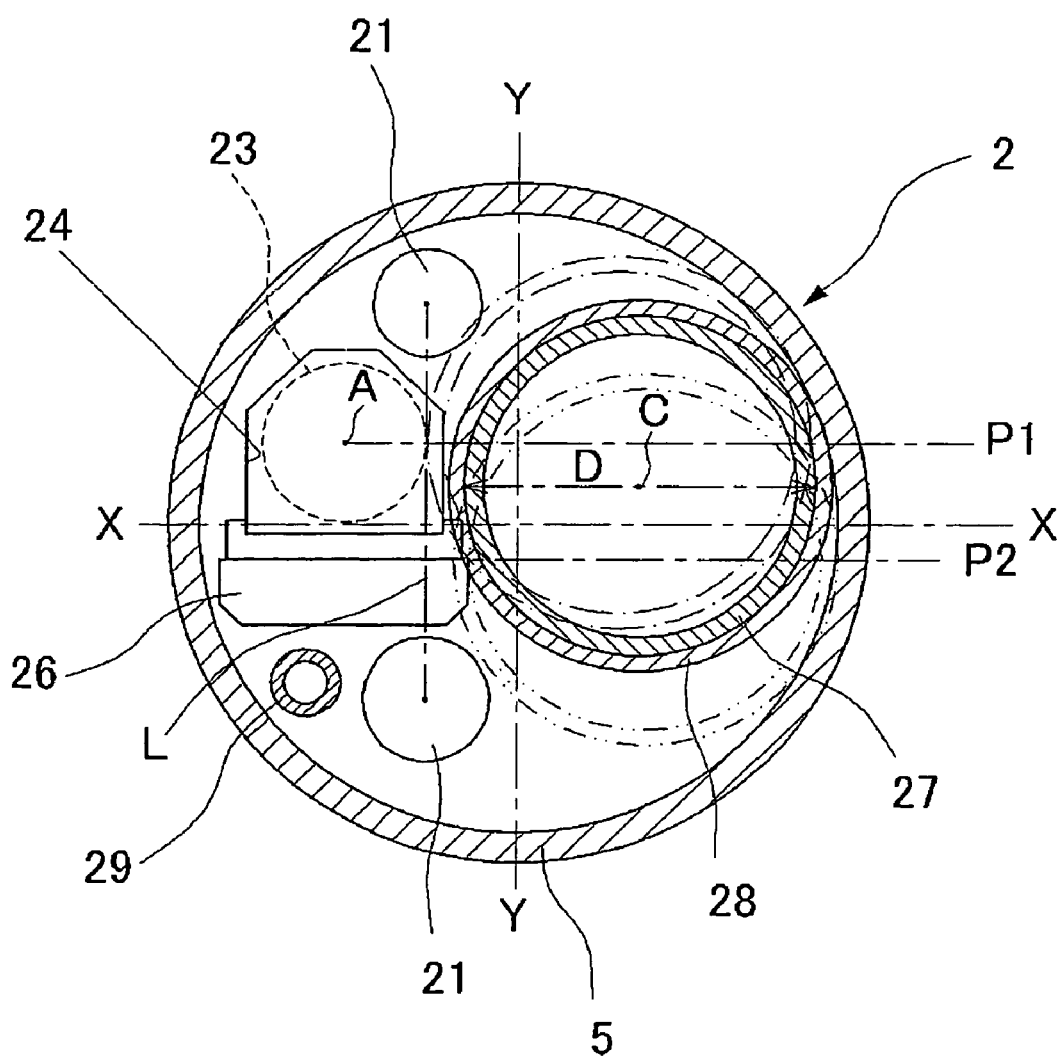
FIG. 4 is a sectional view taken along the line b-b.

A description is given of a detailed structure employed for the above, based on FIG. 4. Herein, on a section orthogonal to the axial line Z-Z of the distal end hard portion 2a, two orthogonal lines X and Y are established, the origin of which is the position of the axial center thereof. The X-axis is the center line of curvature in the vertical direction, and the Y-axis is the center line of curvature in the left and right direction. The bending portion 2b is curved in the vertical direction centering around the X-axis, and is curved in the left and right direction centering around the Y-axis.

The observation portion 11 in which the object optical system and the solid-state pickup device are integrally incorporated, and the treatment equipment lead-out port 12, in detail, the linkage pipe 27 attached to the treatment equipment lead-out port 12, are disposed at both sides between which the Y-axis is placed. In addition, these members 11 and 27 are not necessarily completely accommodated in a semicircular area at both sides of the Y-axis, where if a majority thereof is positioned in the area, they may more or less protrude into the other area.

In the construction shown in FIG. 4, in the observation portion 11, the widest portion is the substrate 26 in which the solid-state pickup element 25 is incorporated. And, the incorporated surface on which the solid-state pickup element 25 of the substrate 26 is mounted is disposed so as to be faced in the direction parallel to the X-axis. In addition, where it is assumed that the center of the optical axis of the object lens 23 is A, and the plane including the surface of the substrate 26 and parallel to the X-axis is P, the center A of the optical axis of the object lens 23 and the plane P of the substrate 26 are disposed at both sides between which the X-axis is placed. Further, the position of the observation portion 11 is as apart from the Y-axis as possible under the condition that the observation portion 11 does not interfere with the inner surface of the distal end sleeve 5 of the distal end hard portion 2a.

Next, with respect to arrangement of the illumination portions 10 and 10 provided at two points, line L is disposed roughly in parallel to the Y-axis where it is assumed that the line connecting the centers of both the illumination portions 10 and 10 to each other is L. In addition, the line L is drawn near the center A of the optical axis of the object lens 23. Further, the distances between the center A of the optical axis and both the illumination portions 10 and 10 are made as equal to each other as possible. Therefore, both the illumination portions 10 are in an area at the side where the observation portion 11 is disposed and are positioned upward and downward of the observation portion 11. And, as depicted, if there is a difference between both the illumination portions 10 and the center A of the optical axis of the object lens 23, the diameter of the illumination portion which is farther from the observation portion is made larger than the diameter of the illumination portion which is nearer thereto.

Further, the position of the treatment equipment lead-out portion 12 disposed at the area opposite the observation portion 11 with the Y-axis placed therebetween is determined so that the center C of the linkage pipe 27 is disposed, in the Y-axis direction, between the plane P1 parallel to the X-axis including the center A of the optical axis of the object lens 23 and the plane P2 of the substrate 26. And, the feeding tube 30 connected to the rinsing fluid passage 29 communicating with the rinsing nozzle 13 is disposed at the lower position of the substrate 26.

By composing the members as described above, it becomes possible to form the treatment equipment lead-out port having a large diameter in addition to making the distal end hard portion 2a smaller in diameter. That is, as depicted in FIG. 4, the linkage pipe 27 attached to the treatment equipment lead-out port 12 is caused to have the maximum diameter under the conditions that the linkage pipe 27 does not interfere with the inner surface of the distal end sleeve 5 of the distal end hard portion 2a and respective parts composing the observation portion 11. Herein, in FIG. 4, since the center C of the treatment equipment lead-out port 12 is disposed between the plane P1 parallel to the X-axis including the center A of the optical axis of the object lens 23 and the plane P2 including the surface of the substrate 26, the diameter of the linkage pipe 27 fitted to the treatment equipment lead-out port 12 can be made into a dimension depicted with D in FIG. 4.

However, where the center C of the treatment equipment lead-out port 12 is positioned upward from the plane P1 in the drawing, if the linkage pipe 27 having diameter D is mounted, it interferes with the inner surface of the distal end sleeve 5 of the distal end hard portion 2a depicted with a one-dashed chain line in the same drawing, and if the center C is positioned downward of the plane P1, it interferes with the inner face of the distal end sleeve 5 as depicted with a two-dashed chain line in the same drawing. Therefore, unless the diameter of the treatment equipment lead-out port 12 is made smaller, the linkage pipe 27 cannot be mounted.

By composing these members as described above, even if the distal end hard portion 2a is made smaller in diameter, the diameter of the treatment equipment lead-out port 12 can be made large. Furthermore, almost equal illumination light will be able to be irradiated centering around the observation center A. As described above, the line L connecting the centers of the illumination portions 10 and 10 secured at two points is roughly parallel to the Y-axis, and is drawn near the center A of the optical axis of the object lens 23, and further the distances between the center A of the optical axis of the object lens 23 and both the illumination portions 10 are almost equal to each other. Therefore, it becomes possible to irradiate light with almost uniform light intensity over the entire observation field of vision from the extension line of the observation center A in the observation portion 11. As a result, since unevenness in the illumination light will hardly occur with respect to an object image in the pickup range, the quality of images obtained by the solid-state image pickup device 25 can be remarkably improved. Accordingly, it becomes possible to carry out inspections and diagnoses at high accuracy, using the endoscope.

As described above, by making large the treatment equipment lead-out port and the treatment equipment insertion channel connected thereto, large-sized treatment equipment can be inserted, and the distal end hard portion can be made smaller in diameter. Further, unevenness in illumination from a pair of illumination portions, which are provided with the observation portion placed therebetween, can be suppressed to the minimum, wherein clear images can be acquired.

The entire disclosure of each and every foreign patent application from which the benefit of foreign priority has been claimed in the present application is incorporated herein by reference, as if fully set forth.

What is claimed is:

1. An endoscope comprising:
a body control portion; and
an insertion portion including a distal end hard portion, the insertion portion being connected to the body control portion,
wherein an endoscope observing section and a treatment equipment lead-out port are provided at a distal end surface of the distal end hard portion, the endoscope observing section comprising two illumination portions and an observation portion, and
wherein the observation portion comprises:
an object optical system comprising an object lens and a prism for bending an optical axis of the object lens by 90° and;
a pickup assembly comprising a solid-state image pickup device and a substrate of the solid-state image pickup device, the pickup assembly being connected to the prism, and
wherein at least one of the illumination portions comprises an illumination lens and a light guide disposed opposite the illumination lens,
wherein, when first and second axes orthogonal to each other are established on a section orthogonal to an axial line of the distal end hard portion, the first and second axes centering around an axial center of the distal end hard portion, the pickup assembly is disposed so as to be oriented to a direction parallel to the first axis, and the pickup assembly and an observation center of the object lens are disposed opposite each other with the first axis placed therebetween;
the treatment equipment lead-out port and the observation portion are disposed opposite each other with the second axis placed as a boundary therebetween;
a center of the treatment equipment lead-out port is disposed at a position between a first plane including a surface of a portion at the maximum width of the pickup assembly, and a second plane including the observation center of the object lens, the second plane being parallel to the first plane;
the illumination portions are disposed on opposite sides of the object lens and each of the illumination portions is disposed at a side where the object lens is disposed with respect to the second axis; and
the surface of the portion at the maximum width of the pickup assembly is a light-receiving plane of the solid-state image pickup device.

2. The endoscope according to claim 1,
wherein the insertion portion further comprises a bending portion connected to the distal end hard portion, and
the bending portion is bendable in four directions including upward, downward, leftward and rightward, and the first axis is a center axis for bending in the up and down directions, and the second axis is a center axis for bending in the left and right directions.

3. The endoscope according to claim 1, wherein the two illumination portions are disposed so that a virtual line connecting centers of the two illumination portions is substantially parallel to the second axis.

* * * * *